(12) United States Patent
Glazer

(10) Patent No.: US 9,530,080 B2
(45) Date of Patent: Dec. 27, 2016

(54) SYSTEMS AND METHODS FOR CONFIGURING BABY MONITOR CAMERAS TO PROVIDE UNIFORM DATA SETS FOR ANALYSIS AND TO PROVIDE AN ADVANTAGEOUS VIEW POINT OF BABIES

(71) Applicant: Assaf Glazer, Hoboken, NJ (US)

(72) Inventor: Assaf Glazer, Hoboken, NJ (US)

(73) Assignee: Joan and Irwin Jacobs Technion-Cornell Institute, New York, NY (US)

( * ) Notice: Subject to any disclaimer, the term of this patent is extended or adjusted under 35 U.S.C. 154(b) by 0 days.

(21) Appl. No.: 14/681,573

(22) Filed: Apr. 8, 2015

(65) Prior Publication Data

US 2015/0288877 A1 Oct. 8, 2015

Related U.S. Application Data

(60) Provisional application No. 61/976,666, filed on Apr. 8, 2014.

(51) Int. Cl.
| | |
|---|---|
| *G06K 9/62* | (2006.01) |
| *H04N 7/18* | (2006.01) |
| *G06K 9/00* | (2006.01) |
| *H04N 5/225* | (2006.01) |
| *H04N 5/232* | (2006.01) |
| *H04N 5/33* | (2006.01) |

(52) U.S. Cl.
CPC ......... *G06K 9/6262* (2013.01); *G06K 9/00335* (2013.01); *G06K 9/00771* (2013.01); *H04N 5/2251* (2013.01); *H04N 5/2256* (2013.01); *H04N 5/23206* (2013.01); *H04N 5/33* (2013.01); *H04N 7/183* (2013.01)

(58) Field of Classification Search
CPC .......................... H04N 5/23222; G06K 9/6262
See application file for complete search history.

(56) References Cited

U.S. PATENT DOCUMENTS

| | | | | |
|---|---|---|---|---|
| 6,113,455 | A | * | 9/2000 | Whelan ................ A63H 33/006 |
| | | | | 248/214 |
| 7,035,432 | B2 | | 4/2006 | Szuba |
| (Continued) | | | | |

OTHER PUBLICATIONS

Dalai, Navneet Histograms of Oriented Gradients for Human Detection. Proceedings of the 2005 IEEE Computer Society Conference on Computer Vision and Pattern Recognition (CVPR'05) 2005 IEEE.

(Continued)

*Primary Examiner* — Jay Patel
*Assistant Examiner* — Irfan Habib
(74) *Attorney, Agent, or Firm* — Seth H. Ostrow, Esq.; Meister Seelig & Fein LLP

(57) ABSTRACT

Systems and methods for monitoring babies with cameras using a centralized computation and storage center that allows using visual output signals for computer vision and machine learning analysis and high-level reasoning of baby movements. The system comprises a camera located at a predefined working point above a baby's crib, and one or more communication networks between components of the system including a web-based network for in-depth computer vision and machine learning analysis of the visual output signals by an analysis server.

16 Claims, 8 Drawing Sheets

(56) References Cited

U.S. PATENT DOCUMENTS

| | | | |
|---|---|---|---|
| 7,277,122 B2* | 10/2007 | Sakai | H04N 5/232 348/143 |
| 7,318,051 B2* | 1/2008 | Weston | G06K 9/6215 706/12 |
| 7,397,380 B1* | 7/2008 | Smolsky | A61B 5/015 340/573.1 |
| 7,470,167 B2* | 12/2008 | Clark | A63H 33/006 340/573.1 |
| 7,477,285 B1 | 1/2009 | Johnson | |
| 7,624,074 B2* | 11/2009 | Weston | G06N 99/005 706/1 |
| 7,696,888 B2 | 4/2010 | Swan et al. | |
| 7,774,032 B2* | 8/2010 | Swan | G08B 13/19621 340/539.15 |
| 7,827,631 B2* | 11/2010 | Holman | A47D 7/03 5/100 |
| 8,461,996 B2* | 6/2013 | Gallagher | A61B 5/113 340/539.12 |
| 8,471,899 B2 | 6/2013 | Johnson | |
| 8,484,774 B2* | 7/2013 | Cohen | A47C 19/045 5/11 |
| 8,638,364 B2 | 1/2014 | Chen et al. | |
| 8,640,280 B2* | 2/2014 | Gutierrez | A47D 7/03 5/100 |
| 8,646,126 B2* | 2/2014 | Carta | A47D 7/03 5/100 |
| 8,675,059 B2 | 3/2014 | Johnson et al. | |
| 8,676,603 B2 | 3/2014 | Johnson et al. | |
| 9,330,343 B2* | 5/2016 | Nakano | G06K 9/6262 |
| 2003/0233806 A1* | 12/2003 | Kuebler | E04H 12/12 52/838 |
| 2005/0285941 A1 | 12/2005 | Haigh et al. | |
| 2007/0285259 A1 | 12/2007 | Desrosiers et al. | |
| 2007/0285570 A1 | 12/2007 | Desrosiers et al. | |
| 2008/0016624 A1* | 1/2008 | Osborn | A63H 33/006 5/658 |
| 2008/0180537 A1 | 7/2008 | Weinberg et al. | |
| 2008/0309765 A1* | 12/2008 | Dayan | H04N 7/185 348/158 |
| 2009/0066671 A1* | 3/2009 | Kweon | G06F 3/0421 345/175 |
| 2009/0091617 A1 | 4/2009 | Anderson | |
| 2009/0278934 A1 | 11/2009 | Ecker et al. | |
| 2010/0060448 A1* | 3/2010 | Larsen | A63H 33/006 340/539.15 |
| 2010/0202659 A1 | 8/2010 | Hamalainen | |
| 2010/0241018 A1 | 9/2010 | Vogel | |
| 2011/0044533 A1* | 2/2011 | Cobb | G06K 9/00771 382/155 |
| 2011/0118608 A1 | 5/2011 | Lindner et al. | |
| 2011/0261182 A1 | 10/2011 | Lee et al. | |
| 2011/0295583 A1 | 12/2011 | Hollock et al. | |
| 2011/0310247 A1* | 12/2011 | Rensin | H04L 29/06027 348/143 |
| 2011/0313325 A1* | 12/2011 | Cuddihy | G08B 21/0476 600/595 |
| 2012/0075464 A1 | 3/2012 | Derenne et al. | |
| 2013/0072823 A1* | 3/2013 | Kahn | |
| 2013/0169735 A1* | 7/2013 | Barker | G08B 21/0261 348/14.02 |
| 2013/0182107 A1 | 7/2013 | Anderson | |
| 2013/0241730 A1* | 9/2013 | Saitwal | H04N 7/002 340/540 |
| 2013/0250063 A1 | 9/2013 | Lee et al. | |
| 2014/0072206 A1* | 3/2014 | Eaton | G06K 9/00335 382/159 |
| 2014/0092247 A1 | 4/2014 | Clark et al. | |
| 2014/0121540 A1* | 5/2014 | Raskin | A61B 5/6898 600/479 |
| 2014/0168397 A1 | 6/2014 | Greco et al. | |
| 2014/0204207 A1 | 7/2014 | Clark et al. | |
| 2014/0247334 A1 | 9/2014 | Johnson et al. | |
| 2014/0267625 A1 | 9/2014 | Clark et al. | |
| 2014/0270494 A1 | 9/2014 | Sawhney et al. | |
| 2014/0288968 A1 | 9/2014 | Johnson | |
| 2014/0334058 A1* | 11/2014 | Galvan | F41H 13/0025 361/232 |
| 2015/0109441 A1* | 4/2015 | Fujioka | H04N 7/183 348/143 |
| 2016/0183695 A1* | 6/2016 | Veron | A47D 9/00 340/573.1 |

OTHER PUBLICATIONS

Derpanis, Konstantinos G. "Overview of the RANSAC Algorithm." York University 68 (2010).

Felzenszwalb, Pedro F. Object Detection with Discriminatively Trained Part Based Models. Pattern Analysis and Machine Intelligence, IEEE Transactions on (vol. 32 , Issue: 9, pp. 1627-1645) Sep. 2009.

Glazer, Assaf et al., One-Class Background Model. ACCV 2012 Workshops, Part I, LNCS 7728, pp. 301-307 2013.

Viola, P.; et al. Rapid Object Detection Using a Boosted Cascade of Simple Features Mitsubishi Electric Research Laboratories May 2004 pp. 1-9.

Viola, Paul. Rapid Object Detection using a Boosted Cascade of Simple Features. Computer Vision and Pattern Recognition, 2001. CVPR 2001. Proceedings of the 2001 IEEE Computer Society Conference on (vol. 1 pp. I-511-I-518).

Weinland, Daniel. A Survey of Vision-Based Methods for Action Representation, Segmentation and Recognition. Institut National De Recherche En Informatique Et En Automatique. Version 1—Feb. 24, 2010.

Ronald Poppe. Vision-based human motion analysis: An overview. Computer Vision and Image Understanding 108 (2007) 4-18.

Thomas B. Moeslund and Erik Granum. A Survey of Computer Vision-Based Human Motion Capture. Computer Vision and Image Understanding 81, 231-268 (2001).

Julie A. Kientz and Gregory D. Abowd. KidCam: Toward an Effective Technology for the Capture of Children's Moments of Interest. Pervasive 2009, LNCS 5538, pp. 115-132, 2009.

Kam-Yiu Lam and Calvin K. H. Chiu. Mobile Video Stream Monitoring System. Proceedings of the 11th ACM International Conference on Multimedia, Nov. 2-8, 2003.

* cited by examiner

SYSTEMS AND METHODS FOR CONFIGURING BABY MONITOR CAMERAS TO PROVIDE UNIFORM DATA SETS FOR ANALYSIS AND TO PROVIDE AN ADVANTAGEOUS VIEW POINT OF BABIES

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

CROSS REFERENCE TO RELATED APPLICATION

This application claims the priority of U.S. Provisional Application No. 61/976,666, entitled "SYSTEMS AND METHODS FOR MONITORING BABIES," filed on Apr. 8, 2014, the disclosure of which is hereby incorporated by reference in its entirety.

BACKGROUND OF THE INVENTION

Field of the Invention

The present invention related generally to systems and methods for baby monitoring, and specifically to systems and method using cameras in monitoring babies in their cribs.

Description of the Related Art

Baby monitor cameras are commonly used to watch over babies from afar. By looking at the monitor, parents can check their baby's condition without being present next to their crib. Baby monitor cameras entered the market around 1993. The traditional baby monitors consist of a camera and a remote monitor. The camera is placed near the child and its video signal is transmitted by radio waves to the remote monitor. Most baby monitor cameras have also an infrared (IR) vision sensor to allow monitoring at night.

During the 2000s, with the introduction of personal computers into every home, parents started to use wireless Internet Protocol (IP) cameras for baby monitoring. (IP cameras had been used till then mainly for security reasons.) However, these parents were a small market since wireless IP cameras have to be configured to operate on a home network, which make them more complicated to install and maintain for parents. In addition, IP cameras can be hacked easily when connected to the Internet without taking extra security steps to secure them.

Today, baby monitor cameras offer various high-tech features, such as high-definition (HD) resolution, easy setup, secured connection, recording capabilities, 2-way audio, notifications on baby cry and/or movements, lullaby playing, control of multiple cameras, video over Skype, etc. Some of them are also equipped with additional non-vision-based sensors, e.g., movement sensor, temperature, heart/breath listener, and IR motion detector. As a result, many useful tasks that require in-depth analysis of image sequences cannot be performed, including, for example, creating a video summary of a baby's activities and development over time. Current baby monitor cameras also cannot use image sequences from multiple baby monitor cameras to detect abnormal baby movements and behaviors. It is therefore desirable to provide baby monitor cameras capable of handling a large amount of images sequences to allow data analysis and high-level reasoning of baby movements.

Another shortcoming of current baby monitor cameras is finding an appropriate place to put the baby monitor camera around the crib. Examples include (1) trying to put it on a shelf, but the view of the baby is from too shallow of an angle, too far of a location (bad resolution), and sometimes the baby is hidden by the rungs; (2) putting it on a higher shelf in the closet, next to the crib, but have to keep the closet door open at all times; (3) parents think about mounting the camera to the wall, but find it is too messy and also afraid power cable would damage the appearance of the baby's room; and (4) parents using tape to mount the camera to the rungs (which can be dangerous as the cable can go inside the crib). As such, there is a need for a better configuration and location of baby monitor cameras.

SUMMARY OF THE INVENTION

The present invention provides a system for monitoring a baby. The system comprises a camera configured at a predefined working point above a baby crib to obtain visual output signals, and a network interface controller configured to transfer the visual output signals to client devices, and transfer the visual output signals to an analysis server, the analysis server configured to perform computer vision and machine learning analysis on the visual output signals, compare the computer vision and machine learning analysis to comparative data, correlate the computer vision and machine learning analysis to events based on the comparison, and transmit messages based on the events correlating to the computer vision and machine learning analysis to the client devices.

The camera may be configured to transfer the visual output signals to client devices over a local area network. In another embodiment, the camera is configured to transfer visual output signals to the analysis server over a web-based network connected to a centralized computation and storage center. The camera and the predefined working point can be substantially the same for monitoring different babies.

The analysis server may be further configured to generate notifications based on the computer vision and machine learning analysis and transmit the notifications to the client devices. According to a further embodiment, the notifications include baby waking up, baby falling asleep, baby self-soothes. The analysis server may also be further configured to generate alerts based on the computer vision and machine learning analysis, and transmit the alerts based on the computer vision and machine learning analysis. The alerts may include baby rolled over, baby is crying, baby is climbing, baby spits up, foreign object in crib, aspiration event, flip event, seizures event, leg stuck event, and head covered event. In another embodiment, the analysis server is further configured to perform computer vision and machine learning processing on the visual output signals as part of performing the computer vision and machine learning analysis on the visual output signals. The computer vision and machine learning processing may include at least one of background subtraction algorithms, baby region of interest detection, head detection processes, parental intervention detection, behavioral classification, action rectangle identification, hands detection, and baby presence detection methods.

According to another embodiment of the present invention, the system comprises an analysis server configured to receive visual output signals from camera systems, analyze the visual output signals by identifying features in the visual output signals using computer vision and machine learning, compare the identified features to comparative data, correlate the identified features to events based on the comparison, and transmit messages based on the events correlating to the identified features to client devices associated with the camera systems.

In yet another embodiment, the system comprises a camera configured at a predefined working point above a crib to obtain visual output signals from the predefined working point, the camera comprising a camera housing including a lens, infrared light emitting diodes (IR LED) lights, a light sensor, and power and data cabling. The system also comprises a mount including an upper arm connected to the camera housing, the upper arm including a first interior conduit configured to receive the power and data cabling of the camera housing, a lower arm connected to the upper arm, the lower arm including a second interior conduit configured to receive the power and the data cabling of the camera housing from the upper arm, and a crib attachment configured to attach the mount to the crib at the predefined working point above the crib. The system further comprises a network interface controller configured to transfer the visual output signals from the predefined working point to an analysis server, the analysis server configured to perform computer vision and machine learning analysis on the visual output signals from the predefined working point, compare the computer vision and machine learning analysis to comparative data, correlate the computer vision and machine learning analysis to events based on the comparison, and transmit messages based on the events correlating to the computer vision and machine learning analysis to client devices.

The light sensor may be configured on the camera to sense the intensity of ambient light and infrared light from the IR LED lights. The IR LED light may be further configured by a processor based on the intensity of ambient light and infrared light from the IR LED lights. One embodiment includes the camera utilizing infrared (IR) filters to filter IR light. The IR LED lights may include a wavelength of approximately 850 nm to 940 nm such that a red glare is not visible to a baby lying under the camera.

According to one embodiment, the upper arm includes at least one of speakers, night lights, temperature and humidity sensors. The camera housing may further include a lens mount operable for positioning with a rotational adjustment of 15 degrees of pan along a horizontal axis relative to the crib. In another embodiment, the camera housing is configured to allow the camera to rotate 15 degrees of pan relative to the upper arm. The mount may also be attached to an outer side of the crib. One embodiment includes the system having a sensitive white night light configured on the top, outer side of the upper arm, and directed away from an underside of the camera and upwards towards a ceiling. The mount may also comprise a universal mount with a bird's-eye view.

The capabilities of current baby monitor camera systems to perform data analysis and high-level reasoning of baby movements from image sequences are relatively poor. The reason for that is mainly the complexity of solving computer vision tasks in non-stationary setups, where baby monitor cameras are located in different locations and orientations around the baby. Computer vision tasks in these setups are hard to solve since they can have multiple moving objects at different scale and poses, and with potential hidden parts that need to be modeled. However, the baby monitor camera system including a mount according to embodiments of the present invention provides a solution to these issues.

BRIEF DESCRIPTION OF THE DRAWINGS

The invention is illustrated in the figures of the accompanying drawings which are meant to be exemplary and not limiting, in which like references are intended to refer to like or corresponding parts, and in which.

DETAILED DESCRIPTION OF THE INVENTION

Figure 1A:
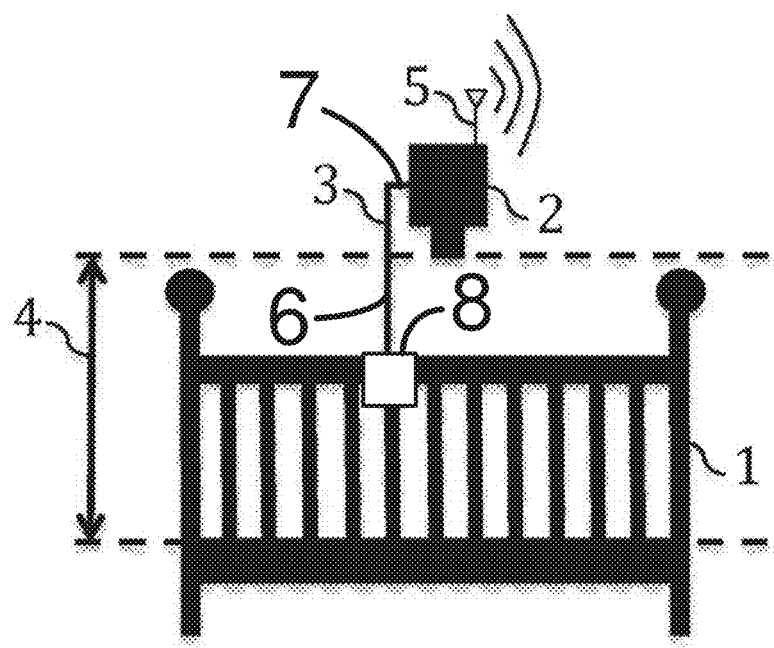
FIG. 1A illustrates a baby monitor camera configuration with a baby's crib in accordance with an embodiment of the present invention.

Subject matter will now be described more fully hereinafter with reference to the accompanying drawings, which form a part hereof, and which show, by way of illustration, exemplary embodiments in which the invention may be practiced. Subject matter may, however, be embodied in a variety of different forms and, therefore, covered or claimed subject matter is intended to be construed as not being limited to any example embodiments set forth herein; example embodiments are provided merely to be illustrative. It is to be understood that other embodiments may be utilized and structural changes may be made without departing from the scope of the present invention. Likewise, a reasonably broad scope for claimed or covered subject matter is intended. Among other things, for example, subject matter may be embodied as methods, devices, components, or systems. Accordingly, embodiments may, for example, take the form of hardware, software, firmware or any combination thereof (other than software per se). The following detailed description is, therefore, not intended to be taken in a limiting sense. Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of exemplary embodiments in whole or in part.

Embodiments of the present invention that are described herein provide a baby monitor camera system including baby monitor cameras that allow using the cameras' output signal for data analysis and high-level reasoning of baby movements. The described system includes a novel infant monitoring system for ensuring an infant's safety while the caretakers (e.g., parents, grandparents, nannies, babysitters, and the like) are not in the room with the infant while allowing peace of mind for the caretaker, and helping parents to validate "non-intervention" decision. That is, embodiments of the present invention help parents/caretakers decide when they don't need to intervene. Hardware in the system includes cameras, temperature and humidity sensors, two-way audio, IR night vision, nightlight, and IR LEDs illumination that can be configured to provide live stream and cloud recording of the baby's crib sleeping environment. According to some embodiments, computer vision generated video summaries of events may be provided in simple, short clips that can be shared with friends and family on social media as desired. Time-lapsed video summaries, sharable moments (that can be shared on social networking), notification and actionable alerts, sleep tracking and training, personalized parenting tips, tracking development milestones, and smart home integration may also be provided.

By using computer vision and machine learning technologies, the baby monitor camera system is able to provide parents and caretakers with actionable alerts and personalized data on a child's development. The present invention may also utilize computer vision algorithms on videos of multiple babies to give parents and caretakers personalized insights, which are based on comparison between multiple babies. The present invention can provide parents and caretakers with information they want to know such as whether a baby's development is normal, a baby's sleep is normal, if the parents or caretakers are approaching the crib as normal, or if a baby is safe. Other additional features may include baby metrics and percentiles, network patterns and insights, abnormalities database, early disease detection, information on Sudden Infant Death Syndrome (SIDS), new visual language of baby behavior, and telemedicine. The system may send an alert to parents/caretakers if a child is in danger (e.g. a blanket is over the baby's head), benchmark a child's development in comparison to other children within a network, and screen for potential abnormalities. A network of children may comprise a plurality of babies that are identified with same or similar waking patterns, sleeping hours, and sleeping characteristics (e.g., snoring), etc., based on analysis of recorded video data.

In another embodiment, the network may be a social network of parents, caretakers, or users of the baby monitor camera system. The term "social network" refers generally to a network of individuals, such as acquaintances, friends, family, colleagues, or co-workers, coupled via a communications network or via a variety of sub-networks. Potentially, additional relationships may subsequently be formed as a result of social interaction via the communications network or sub-networks. A social network may be employed, for example, to identify additional connections for a variety of activities, including, but not limited to, dating, job networking, receiving or providing service referrals, content sharing, creating new associations, maintaining existing associations, identifying potential activity partners, performing or supporting commercial transactions, or the like. A social network may include individuals with similar experiences, opinions, education levels or backgrounds.

An individual's social network may refer to a set of direct personal relationships or a set of indirect personal relationships. A direct personal relationship refers to a relationship for an individual in which communications may be individual to individual, such as with family members, friends, colleagues, co-workers, or the like. An indirect personal relationship refers to a relationship that may be available to an individual with another individual although no form of individual to individual communication may have taken place, such as a friend of a friend, or the like. Different privileges or permissions may be associated with relationships in a social network. A social network also may generate relationships or connections with entities other than a person, such as companies, brands, or so called 'virtual persons.' An individual's social network may be represented in a variety of forms, such as visually, electronically or functionally. For example, a "social graph" or "socio-gram" may represent an entity in a social network as a node and a relationship as an edge or a link.

Referring to FIG. 1, the baby monitor camera system may comprise a baby crib 1, where the baby is, mount 3, and a camera 2 with a network interface controller 5. Camera 2 may include an image sensor, optics components, main video processing components, lens and lens mount, light sensor, infrared (IR) light-emitting diodes (LEDs), and associated filters (such as IR filters) and mask, microphone, speakers, night light, an indicator light, and power and/or data cable, wiring, or connections. According to other embodiments, the aforementioned components included in camera 2 may be embodied on other hardware within the baby monitor camera system such as on a PCB or computing device. The image sensor may support various resolutions such as 1920×1080 ("1080p"), 1280×720 pixels resolution ("720p"), etc. The image sensor may be sensitive to low light conditions in order to minimize the need of IR LEDs as much as possible. The image sensor may also be oriented in proportion with a crib mattress orientation (assuming camera is configured to the long axis of crib).

A light sensor may also be incorporated into the camera in order to sense the intensity of the ambient and/or IR light from the IR LEDs. The light sensor can be located near the lens in order to provide more accurate readings of the field of vision of the camera 2. Camera 2 may include a plurality (e.g., six to eight) of IR LEDs (e.g., 850 nm-940 nm wavelength) incorporated into camera 2 in an array around the lens to get maximal and uniform light coverage. The IR LEDs may be invisible to the human eye (e.g., no red glow) when in operation so that camera 2 can be less noticeable by the baby. IR illumination from IR LEDs of specific wavelengths, particularly 940 nm, is not used in existing baby monitor cameras. Typically, objects that are 8-10 feet afar from the camera cannot be seen with 940 nm (without a large amount of illumination). However, according to embodiments of the present invention, 940 nm can be used since objects are less than approximately a meter afar from the camera 2. The IR LEDs can be controlled by a main processor, which using readings from the light sensor and/or the image sensor, and can decide whether to operate the IR LEDs or not, and at what intensity. One or more IR filters may be used to allow filtering of IR light during daytime (in the presence of day light) for bright scenes (e.g., part of an actuator/exchanger that will allow inserting or removing the filter according to light sensor readings). The IR filter actuator/exchanger may be of power saving type, requiring power at time of switching the filter status.

According to one embodiment, the lens may be of type M12 and placed on a M12 mount. The lens may be suitable to support resolutions to fit the image sensor. The lens may have a wide-angle of view (e.g., 120-130 degrees horizontal and 150-160 degrees diagonal) in order to cover the area of the crib plus some margins for detection of "parental intervention" and configured to a specific focus (in some embodiments, the user will not be able to change the focus). The specific focus may be a focus that provides a good focus at a plurality of crib mattress positions and at both visible light and IR light conditions. The specific focus may be configured such that a predefined area or field of view of the crib can be captured in a video recording. In some embodiments, focus, exposure, zoom and/or other camera properties of camera 2 may be automatically adjusted based on computer vision and machine learning determination of a crib area in the field of view of the camera. In another embodiment, corrected lens can be used to compensate for the focus shift between day and night vision.

According to an embodiment of the present invention, placement of camera 2 and/or camera properties may be configured to a uniform configuration to establish a same working point such that images from a plurality of baby monitor camera system deployments may be used to reliably compare between image sequences of different babies for computer vision and machine learning analysis. For example, the same camera configuration and the same working point are used for all baby monitor camera systems of different babies in a networked computing environment (such as the one illustrated in FIG. 4). The uniform configuration may also include a height and field of view such that camera 2 won't be disturbed by objects and still able to cover all of crib 1 with its field of view. A centralized computation server, together with the uniform configuration, allows efficient data analysis and high-level reasoning of baby movements. A common camera configuration and working point may be predefined for all baby monitor cameras within the present system such that: the camera is able to capture most/all region where babies move in their crib, and the camera's line of sight would not disturbed by objects that are hanged above the crib, e.g., toys and mobiles. Alternatively, the camera 2 may be positioned in slightly different configurations as long as uniform data sets may be sufficiently collected from multiple cameras to allow data analysis to be performed. The camera may also be configured at a height such that a baby cannot reach the camera. In some embodiments, the camera can be incorporated with a mobile, furniture, or a toy, that is hanged above the crib. For example, referring to FIG. 1D, the baby monitor camera system may include a means for attaching a mobile 10 to mount 3.

A microphone may also be incorporated into camera 2 or mount 3 to capture the baby's sounds and cries. The microphone can be sensitive to sounds at approximately three to four feet away from a zone of interest. For example, the microphone can be configured near the lens of camera 2 in order to ensure being as close to the baby as possible.

Camera 2 may further include a LED indicator light located on the camera housing and pointing upwards (out of the baby's view). The LED can allow for solid and blinking display states, of multiple colors (red, green, yellow, etc.).

Network interface controller 5 may include a Wi-Fi 802.11b/g/n module (including a Wi-Fi antenna) capable of connecting to a home network and/or the Internet. The network interface controller 5 allows users to transmit images captured on camera 2 to a server where they can be analyzed in real-time. The server-side software can then use the analysis to alert loved ones of any issues or dangers that may be occurring or present. Communications to and from camera 2 via network interface controller 5 may be encrypted using WPA2 or any other encryption standard known in the art. The camera 2 may be attach to a crib's vertical rungs, utilizing a standard or universal mounting system similar to crib mobiles including a bird's-eye view, such that camera is oriented in a fixed position above the mattress and out of reach of the child such that parents don't need to struggle with where to mount and put the baby monitor in the room. In the illustrated example, mount 3 is used to place the camera 2 above the crib at the correct working point 4.

In further embodiments, the baby monitor camera system may include temperature sensors to measure room temperature and humidity sensors to measure relative room humidity. According to another embodiment, the system may include a nightlight that can be dimmable by control via a capacitive-touch switch and/or mobile application on a client device. In one embodiment, the nightlights are directed to the ceiling and away from the baby's eyes (underside of the camera) to prevent the baby from being flashed or blinded. The system is capable of broadcasting status and sensory data periodically, e.g., every few seconds to a central or remote server. Status and sensory data may include temperature, humidity, light intensity or brightness, and camera status. These additional features may be either embodied within camera 2 or as separate components communicatively connected to camera 2 and/or network interface controller 5. Electrical components of the baby monitor camera system may be powered by a wall mounted plug-in power supply and cable. In addition, the system may be designed to be portable to the degree that it can be disassembled and reassembled in a new location (e.g. while on vacation or visiting family and friends).

In yet another embodiment, camera 2 may be configured via remote control from a user via the Internet or a local network. Camera 2 allows a remote user to control lighting, IR sensors, video properties (e.g., zoom) and audio properties (e.g., volume). According to another embodiment, camera 2 may be connected to and configured with a smart home system. In such a configuration, a remote user may also control any appliance connected to camera 2 via a smart home system.

Camera 2 may comprise a camera housing having approximate dimensions of 3.5 inches×3.5 inches×3.5 inches. The camera housing may contain an optics printed circuit board (PCB), a main video processing PCB, light sensor, IR LEDs, and associated filters and mask, microphone, an indicator light (e.g., a LED), a lens and a lens mount operable for positioning with a rotational adjustment (e.g., +/−15 degrees of pan) along a horizontal axis (relative to crib 1) utilizing manual controls on the outside of the camera housing. Additionally, the camera housing may allow for camera 2 to rotate (e.g., +/−15 degrees of pan) relative to the mount 3 at upper arm 7.

Figure 1B:
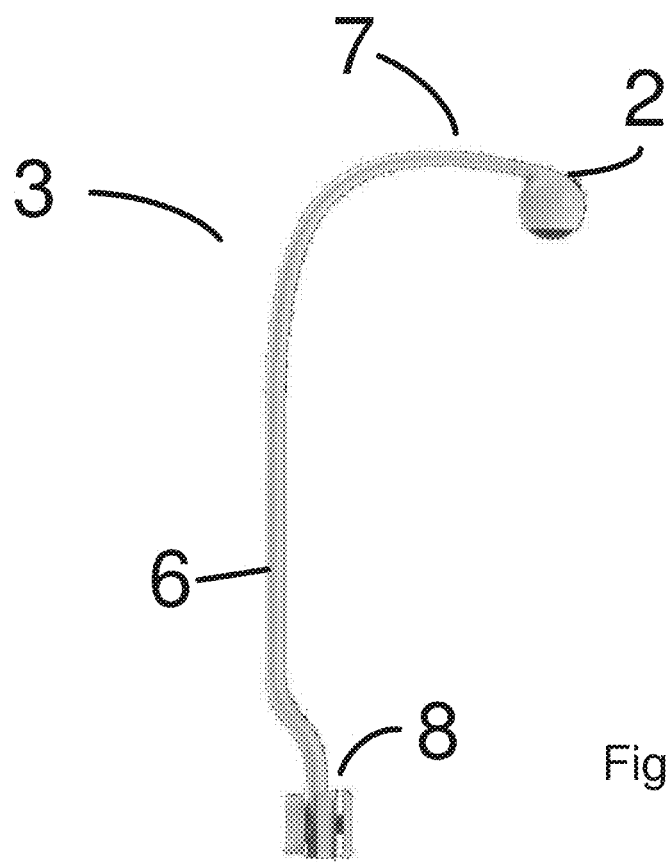
FIG. 1B illustrates a baby monitor camera apparatus in accordance with an embodiment of the present invention.

Referring to FIG. 1B, mount 3 includes lower arm 6, upper arm 7, and crib attachment 8. The upper arm 7 may be a rod or pole having approximate dimensions of 2 inches×13 inches×16.5 inches. One end of upper arm 7 may be attached to the camera housing of camera 2. Upper arm 7 may be constructed to accommodate an internal power and/or data cable from camera 2 via an internal conduit. In certain embodiments, the upper arm 7 may include speakers, night lights (e.g., LED(s)) and associated switch, temperature and humidity sensors, and any associated PCB. Speaker(s) can be incorporated into the upper arm 7 in order to allow "2-way audio" and music or white-noise playback. The speaker(s) may be located in the upper arm 7 pointing inwards, towards the zone of interest. There may be an option to control the volume of the speakers via a switch or by remote control, e.g., via mobile application and device. A LED night light comprising one or more LED lights may be embedded or constructed on the upper arm 7 and projected upwards the ceiling. The intensity can be dimmable, controlled by a capacitive-touch switch or by remote control, e.g., via mobile application and device. Color of the LED night light may be for example, white, soft yellow, daylight, or colored. According to another embodiment, a sensitive white night light may be placed or constructed on the top, outer side of the arm (for example, night light 12 in FIG. 1E). The light may be directed to the ceiling and used for parents/caretakers to see their baby when dark without blinding the baby (e.g., the light illuminates the ceiling and not directed to the child's eye).

The other end of upper arm 7 may be perpendicularly attached to lower arm 6. According to another embodiment, upper arm 7 may transition to the lower arm 6 by a rounded corner. Camera 2 may be joined to mount 3 in a fashion such that upper arm 7 and camera 2 can be horizontally positioned over the crib 1 when lower arm 6 is attached to crib 1 by crib attachment 8 (e.g., to the railing of the crib). The camera 2 may be mounted at heights similar (and below) to that of a mobile such that its line of sight is not obstructed.

Lower arm 6 may have approximate dimensions of 3.5 inches×3.9 inches×12.6 inches. Power and/or data connections may be provided from upper arm 7 to lower arm 6 (e.g., via an internal conduit or cabling system). Power and data cables can be passed through a section of rigid conduit of approximately 17.7 inches in length (mating and contiguous to the lower arm) so that the cable cannot be readily accessed by a child. Power and data may be transferred between the lower arm 6 and upper arm 7 via metal pins, contacts, or jacks in respective mating parts. The lower arm 6 may be configured with a USB connection port and/or an electrical outlet port (connected to the power/data connections and wiring from camera 2 and upper arm 7). In one embodiment, a cable may be connected to the lower arm 6 by use of a USB connector. The USB connector may also allow firmware updates to be completed on the baby monitor camera system.

Figure 1C:
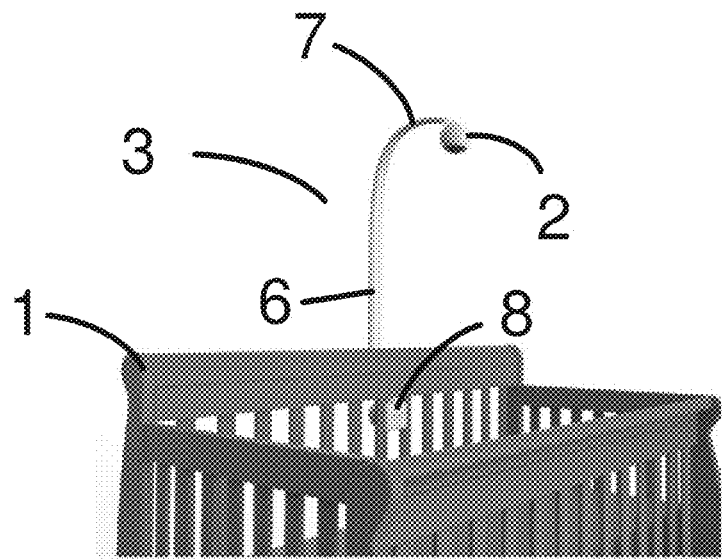
FIG. 1C illustrates a baby monitor camera configuration with a baby's crib in accordance with an embodiment of the present invention.
Figure 1D:
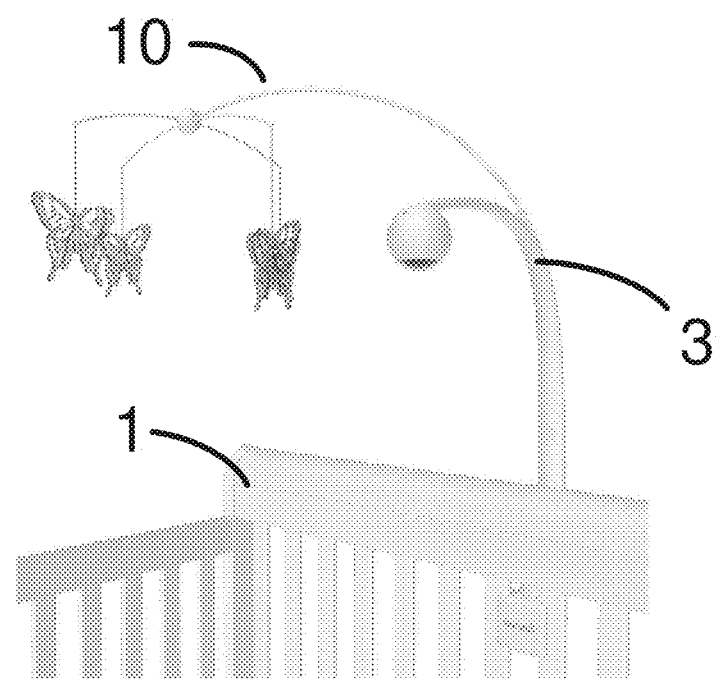
FIG. 1D illustrates a baby monitor camera configuration with a baby's crib in accordance with an embodiment of the present invention.
Figure 1E:
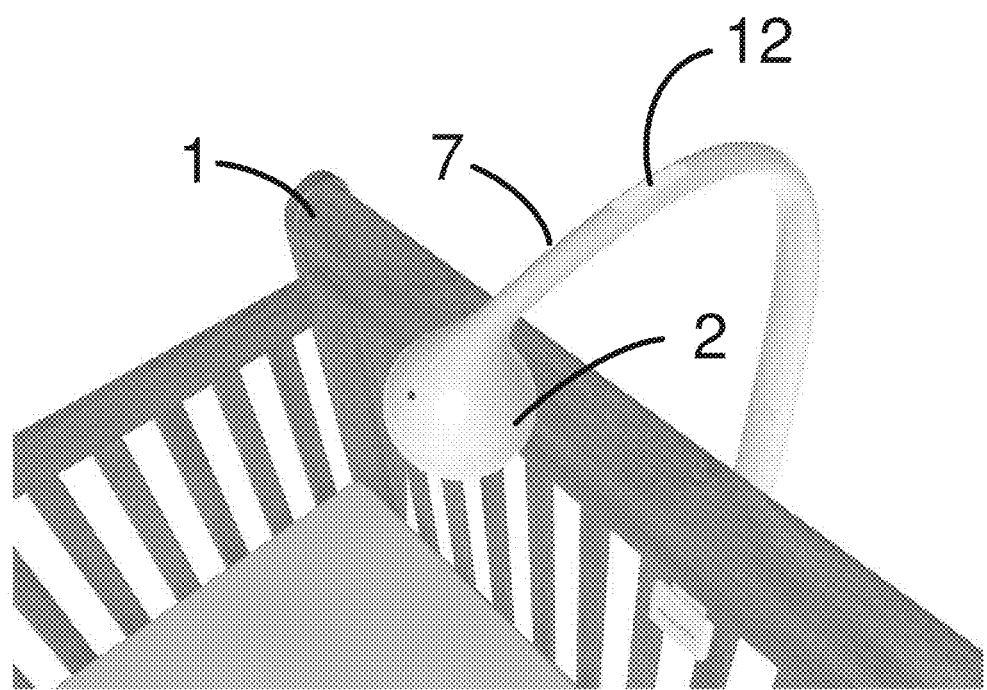
FIG. 1E illustrates a baby monitor camera configuration with a baby's crib in accordance with an embodiment of the present invention.

Lower arm 6 further includes a crib facing mounting surface and/or interface for crib attachment 8. Crib attachment 8 may include one or more mounting bolts keyed for unique orientation that passes through the rails of crib 1 and mounting nuts to fasten the lower arm 6 (at the mounting surface) to the one or more mounting bolts and the crib rails. In some embodiments, one or more portions of mount 3 may accommodate cribs with edges that protrude outwards via an extension or spacer for a predetermined length (e.g., approximately 2 inches) based on a model of the crib. Another embodiment may include a universal mount that solves the problem of where to place the camera. The mounting surface may contain features or material to counteract movement or slippage and to prevent unwanted marking of the crib. The crib attachment 8 may further include a means to configure mount 3 at a specific height (e.g., from the mattress of the crib) and position such that the camera can be configured at a predefined or uniform working point above the crib regardless of the crib model. According to one embodiment, the arm is mounted to the rungs from the outer side of the crib, out of reach of the baby for safety reasons, as illustrated in FIG. 1C.

Figure 2:
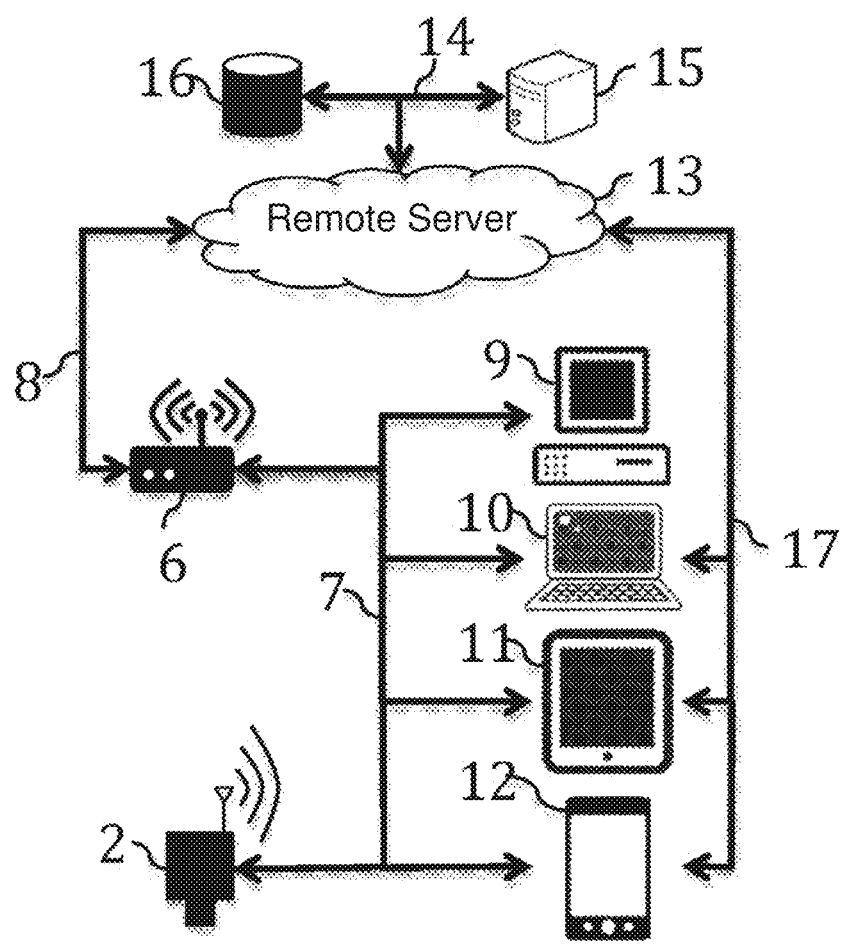
FIG. 2 illustrates a baby monitor camera system in accordance with an embodiment of the present invention.

Referring to FIG. 2, end users such as parents, caretakers, or medical personnel can monitor a baby through of client devices 9, 10, 11, and 12. Client devices 9 through 12 may comprise computing devices (e.g., desktop computers, television set top boxes, terminals, laptops, personal digital assistants (PDA), cell phones, smartphones, tablet computers, e-book readers, smart watches and wearables, or any computing device having a central processing unit and memory unit capable of connecting to a network). Client devices may also comprise a graphical user interface (GUI) or a browser application provided on a display (e.g., monitor screen, LCD or LED display, projector, etc.). A client device may vary in terms of capabilities or features. A client device may also include or execute an application to communicate content, such as, for example, textual content, multimedia content, or the like. A client device may also include or execute an application to perform a variety of possible tasks, such as browsing, searching, playing various forms of content, including locally stored or streamed video.

A client device may include or execute a variety of operating systems, including a personal computer operating system, such as a Windows, Mac OS or Linux, or a mobile operating system, such as iOS, Android, or Windows Mobile, or the like. A client device may include or may execute a variety of possible applications, such as a client software application enabling communication with other devices, such as communicating one or more messages, such as via email, short message service (SMS), or multimedia message service (MMS), including via a network, such as a social network, including, for example, Facebook, LinkedIn, Twitter, Flickr, or Google+, to provide only a few possible examples.

Home network 7 (e.g., Wi-Fi/LAN connection) is operable to communicatively couple camera 2 to devices 9, 10, 11, and 12 via a router 6. A web network 8 (e.g., the Internet) is able to connect members in the home network 7 to the remote server 13 via the router 6. A web network 17 can connect mobile devices 10 through 12 to the remote server 13 via, for example, the Internet. The web network 17 connection may be use when mobile devices 10 through 12 are not members of the home network 7, e.g., when mobile devices are in a remote location outside home.

Users may use client devices to view and see information from their baby monitor camera systems. According to the illustrated configuration, camera 2 may provide for video and/or audio streaming output to a web location or to a local network. The video may be formatted according to any standard and quality, e.g., a MP4 file with H.264 compression, 1280×720 pixels resolution, color video, and a bitrate up to 30 frames per second (fps) for a local network connection, and up to 15 fps for cloud streaming. The video may also be encrypted using an SSL/TSL https protocol, based on AES256 or similar.

The system may allow for variable bitrate and frame rate to reduce amount of data uploaded according to device CPU or capabilities and network upload/download rates. In one embodiment, streaming to a local network may be configured as a live stream using Hypertext Transfer Protocol (HTTP) Live Streaming protocol. The camera 2 may continuously broadcast a data stream on-demand, periodically, on a schedule, or until entering a "sleep mode" (e.g., camera 2 may also stop streaming video/audio when entering sleep mode). Additionally, camera 2 may broadcast sensory data and device status every few seconds to a web location and/or a local network. Sensory data and device status may include room temperature and humidity, light brightness (LED values), and camera status. The sensory data may be viewed when accessing camera 2 from a client device either locally (LAN) or remotely (WAN, Internet, etc.). According to an alternative embodiment, camera 2 may be capable of playback of audio files or streams received from a web location, Internet, WAN, or a local network.

Remote server 13 is capable of connections to multiple baby monitor cameras over the Internet via multiple routers.

The remote sever 13 is capable of handling a large number of image sequences from multiple baby monitor cameras and support multiple end users by using its computing 15 and storage 16 resources. Computing resources 15 may be comprised of servers, mainframes, or any other processing devices. Storage resources 16 may comprise databases, storage devices, and associated hardware. In other embodiments, parts of the data processing and storage components can be found on camera 2, router 6, and/or end user devices 9 through 12 (e.g., mobile device, laptop, home computer). Data streams and other recorded data may be stored on remote server 13 for specified durations such as over the last week, month, etc. The remote server may also include a security system capable of blocking access to the recorded data for devices reported stolen.

Servers described herein are operative to receive requests from client devices and process the requests to generate responses to the client devices across a network. A server may comprise one or more processing components disposed on one or more processing devices or systems in a networked environment. Servers, as described herein, may vary widely in configuration or capabilities but are comprised of at least a special-purpose digital computing device including at least one or more central processing units and memory. A server may also include one or more mass storage devices, one or more power supplies, one or more wired or wireless network interfaces, one or more input/output interfaces, or one or more operating systems, such as Windows Server, Mac OS X, Unix, Linux, FreeBSD, or the like.

The described networks may be any suitable type of network allowing transport of data communications across thereof. The networks may couple devices so that communications may be exchanged, such as between servers, client devices and other types of devices, including between wireless devices coupled via a wireless network, for example. A network may also include mass storage, such as network attached storage (NAS), a storage area network (SAN), cloud computing and storage, or other forms of computer or machine readable media, for example. As discussed above, a network may include or comprise the Internet. Communication on any of the described networks may follow known protocols for data communication. The networks may be configured according to any type of communication network, e.g., local area network (LAN) or wide area network (WAN) connections, cellular networks, wire-line type connections, wireless type connections, or any combination thereof. According to another embodiment, one or more components within the system may communicate with each other via a communications interface, bus, or channel. Communications and content stored and/or transmitted to and from devices may be encrypted using the Advanced Encryption Standard (AES) with a 256-bit key size, and Internet communications may be encrypted using Secure Sockets Layer (SSL) or Transport Layer Security (TLS) protocols, or any other encryption standard known in the art.

Figure 3:
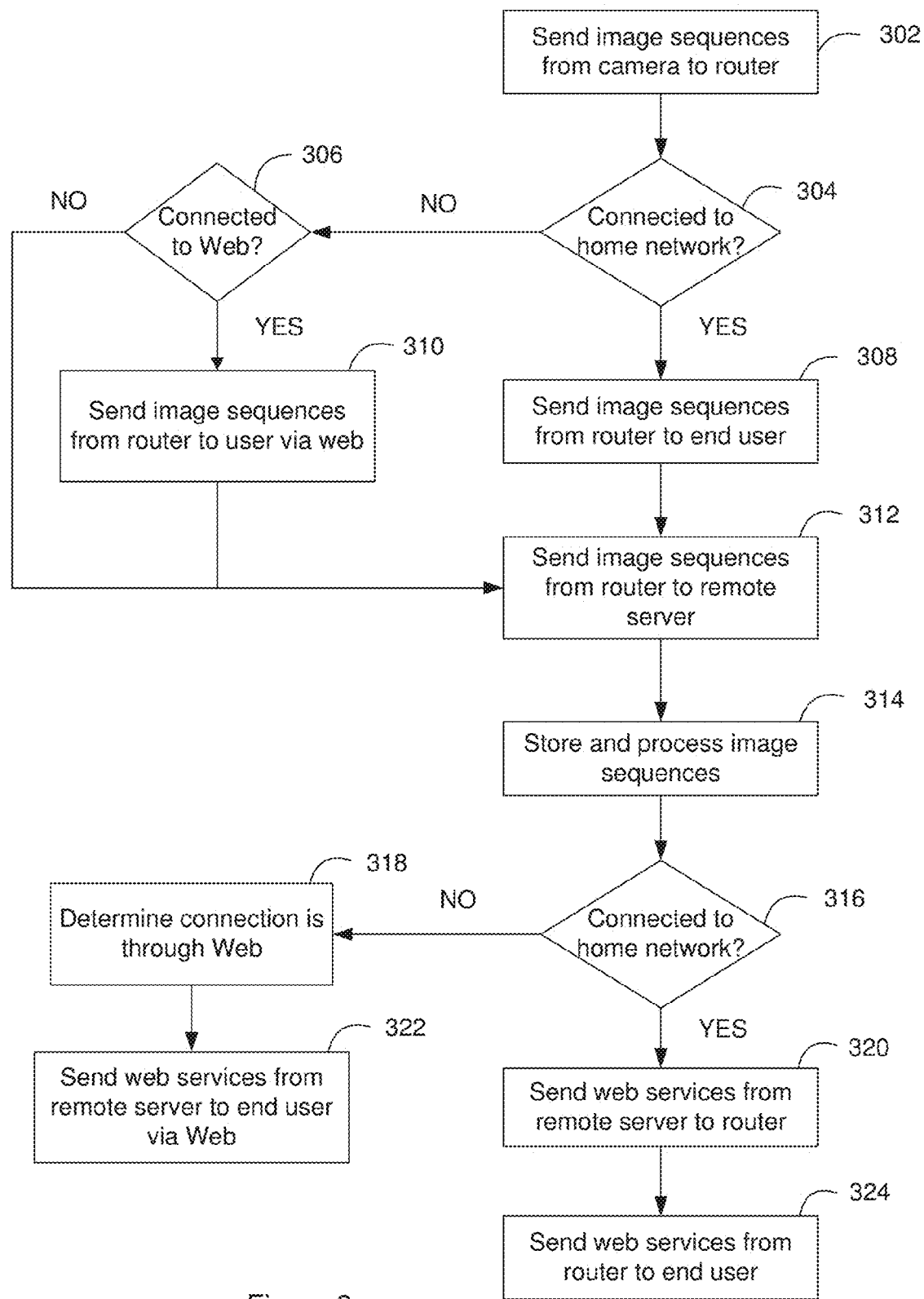
FIG. 3 illustrates a flow chart of a baby monitoring process in accordance with an embodiment of the present invention.

Data transfers from the baby monitor camera system may be achieved in various ways. In one embodiment, as shown in FIG. 3, a method of transferring data between devices in the baby monitor camera system is described. In the method, image sequences (and optionally audio, data from movement sensors, thermometer, heart/breath listener, and IR motion detector) of the baby in his crib are continuously sent from the camera to a router at step 302. If end users are on client devices on a home network 304, then the images sequences are sent from the router to the end users 308. Otherwise, if end users are on client devices connected to the web 306, these image sequences are sent to them via the Internet 310. In both cases, these image sequences are also sent from the router to a remote server 312.

The remote server allows the aggregation of image sequences that are gathered from multiple baby monitor camera systems, thus allowing efficient processing and storage procedures. Image sequences are stored and processed in the remote server 314. This allows for providing services to end users and sharing of videos and images between end users of different baby monitor cameras, that is, of different babies. Services could be, for instance, notifications (e.g., when the baby wakes up, close to waking up, goes to sleep, and self-soothes), actionable alerts (e.g., baby rolled over, baby is crying, baby is climbing, baby spits up, foreign object in crib, aspiration event, flip event, seizures event (e.g., abrupt movements), leg stuck event, or head covered event—these events may be reported in real time if any of these set events occur), achievements (e.g., first time achievements such as longest sleep, moving head from side to side, rolling over, crawling, sitting up, standing, and walking), and baby quantified metrics (e.g., sleep training/tracking, personalized tips—encouraging parent consistency, affecting behavioral changes, redirecting parents to professional assistant, e.g. sleep trainers, and physical measurements). Sharing may be implemented as a social network of end users that use baby monitor cameras. The social network may be established based on third party social networks or a social network provided by a manufacturer of the baby monitor camera system.

According to one embodiment, a remote server may use computer vision and machine learning methods to extract features from baby monitor camera system data, and to perform high-level reasoning techniques of baby movements. Feature may include statistics on when the baby is outside or inside the crib and whether is asleep or awake, statistics on parents/caretakers or other personnel approaching the crib, statistics on child measurements, and statistics on baby movements. For example, providing the parents/caretakers with statistics on sleep patterns over time, showing them a correlation between the hours they put their baby to sleep and the number of hours he slept during the night. Another example may include creating a report of the number of significant movement per night of the baby. A significant movement can be defined, for instance, as a series of movements that last at least ten seconds, where movements between frames are detected in time intervals of at least five seconds. A further example may include creating for the parents or caretakers a report on the number of parental intervention events, that is, the number of times a parent or caretaker approaches the crib during the night, over time. Users may also provide information about the baby such as name, week of birth, date of birth, general diagnosis, gender, and race. The high-level reasoning of baby movements, together with the aggregation of image sequences that are gathered from multiple baby monitor cameras and the sharing of data and information between end-users of different baby camera monitors, allows the extraction of meta-data and reasoning that can improve the sharing experience and screening for abnormalities in accordance with the embodiment of the present invention. For example, common patterns between shared videos of babies pulling, grabbing, or tugging at their ears can be identified and tagged by end users and/or the baby monitor system as a sign of an ear infection. Afterward, when a new, shared video with the similar pattern is received by the remote server, then the system can automatically identify that might be a sign of an ear infection.

The capability of high-level reasoning of baby movements has many other possible applications, as illustrated in the following use cases:

Parents can't figure why their baby cries at night. By utilizing techniques of high-level reasoning for baby movements, parents can monitor abnormal movement patterns, and thus learn why their baby is crying. For instance, abnormal patterns of the baby pulling, grabbing, or tugging at his ears might be a sign of an ear infection.

Parents want to keep updated on their baby's condition when they leave their young one with a babysitter or under medical observation at the hospital. According to an embodiment of the invention, high-level reasoning of baby movements allow parents to receive push notifications to their mobile devices about changes in their child's condition and watch him if necessary when they are not at home/hospital.

Medical staff members need to count the actual number of hours babies sleep in their ward. By high-level reasoning of baby movements, medical personnel can receive daily reports on babies in their ward, which include, for instance, the number of hours the babies sleep.

A supervisor at a daycare center needs to watch for abnormal and satisfactory patterns of babies and nannies behaviors under his supervision. By using high-level reasoning of baby movement and nanny intervention approaches, the supervisor could screen for abnormalities or unsatisfactory nanny behavior. For example, a supervisor will be notified if a nanny didn't approach the crib and watched for the baby for more than a predefined amount of time.

A researcher needs to know the percentage of babies who sleep on their side at the age of 6-9 months. All units of baby monitor cameras are connected to a centralized server, which can thus provide cloud services regarding measurements that were computed in all units. In that sense, the baby monitor camera system serves as a distributed network sensing system and researchers can conduct surveys on babies' development.

Parents, caretakers, and medics want to be alerted when babies are at high risk of SIDS. In one embodiment, non-vision movement sensors can be used to alert parents/caretakers of infants who are at high risk for SIDS. For example, if movements stop, an alarm sounds, giving parents/caretakers critical time to intervene. During the moments before babies stop moving, they show signs of distress that might be identified with a vision sensor, and by adding an image-based signal as input, an increased detection rate for events that are possibly SIDS-related might be obtained.

If end users are members of the home network 316, services data are sent to the router 320 and from there to the end users 324. Otherwise, if end users are connected to the web 318, services data is sent to them via the Internet 322. In other embodiments, data sent between parts of the baby monitor camera system over the home and web networks not only include image sequences and data from services but also other types of data such as messages, notifications, and commands. In some embodiments, baby monitor cameras can be equipped with a 2-way audio sensor and a remote speaker, where an audio signal is transmitted together with the image signal.

Figure 4:
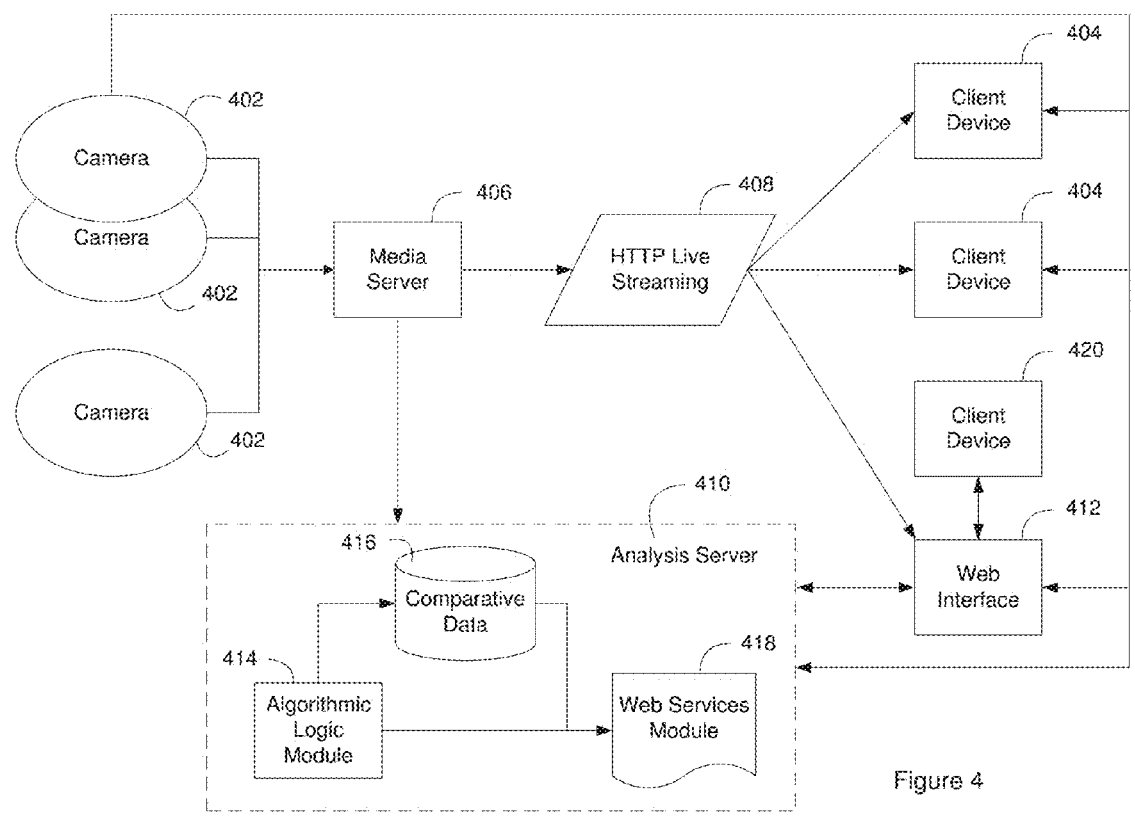
FIG. 4 illustrates a computing system in accordance with an embodiment of the present invention.

FIG. 4 presents a computing system according to an embodiment of the present invention. The illustrated embodiment includes a system comprised of a network of baby monitor camera systems that are communicatively connected to one or more servers and client devices. Cameras 402 are configured to transmit or broadcast data to media server 406 over a WAN connection such as the Internet, cloud, remote network, etc. The plurality of camera 402 may each comprise a baby monitor camera system as described in FIG. 1. The data may include one or more of video, audio, image sequences, temperature data, lighting data, camera device data, etc.

Figure 5:
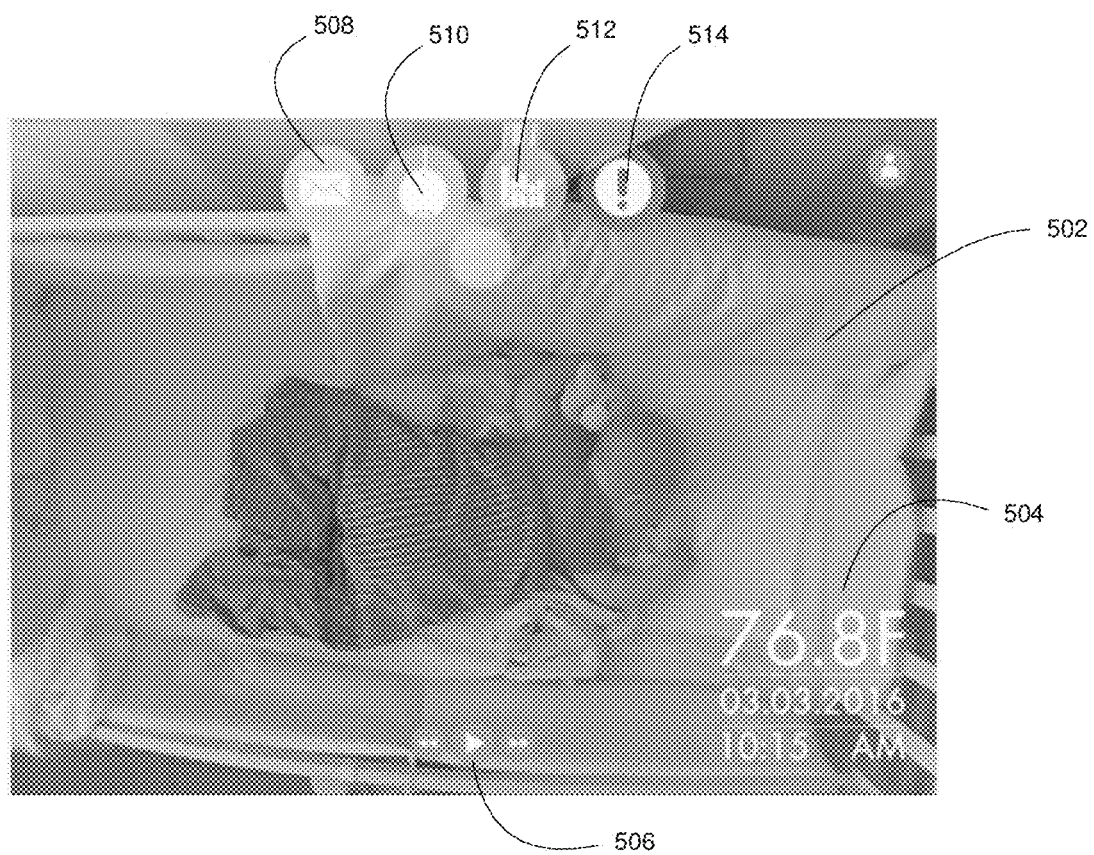
FIG. 5 illustrates an exemplary monitoring interface in accordance with an embodiment of the present invention.

The media server 406 collects the data and may process the data via HTTP live streaming 408 to directly stream video or images to client devices 404 (as an application). Alternatively, client device 404 and client device 420 may access the data stream through a web browser connection to web interface 412. HTTP live streaming 408 provides formatting capabilities to produce live streaming data for download by end users from the data received at media server 406. Live streaming data received by end users at client devices 404 and web interface 412 may comprise a real-time video stream including picture, audio, time, date, temperature, and humidity readings as illustrated in FIG. 5. The real-time video stream may be watched, recorded, paused, and viewed as a time-lapsed video. According to another embodiment, users may be allowed to record video streams directly from their cameras to their client devices (without media server 406 and HTTP live streaming 408) in a configuration where client devices and cameras are connected to a local network. In one embodiment, users may record camera broadcast data to a cloud location.

Media server 406 is also able to send data from cameras 402 to analysis server 410. Analysis server 410 includes algorithmic logic module 414, comparative data database 416, and web services module 418. Image sequences or video of multiple babies may be sent from cameras 402 to analysis server 410, where certain or selected images are processed, stored as comparative data in comparative data database 416 and compared. Other data such as temperature information may also be transmitted from cameras 402 to analysis server 410 for analysis or to supplement the images or video. Analysis server 410 may perform analysis using algorithmic logic module 414 to render web services provided by web services module 418. Results of analysis (online (real-time) or offline) by algorithmic logic module 414 may be used to provide web services requested by end users such as alerts, summaries of activities, and baby profile information. Exemplary services that can be provided by web services module 418 include a video summary of the baby's activities during the night, a video summary of the baby developing over time, directions of where to find the pacifier in the baby's crib when the lights are off, a notification upon request when the baby's head is covered with a blanket, a notification upon request when the baby is awake, a notification upon request when the baby is crying, a notification upon request during the night (e.g., 2-3 minutes in advance), when the baby will wake up, a notification upon request during the daytime (e.g., 2-3 minutes in advance) when the baby will wake up, a notification upon request if the baby sleeps on his back or on his stomach, to name a few. For example, analysis results may be used to display summaries of baby movement, summaries of baby flips, movement over night and/or over a time frame defined by the user, summaries of nursing patterns (e.g., parenting interventions events) over night and/or over a time frame defined by the user, summaries of coughing events over night and/or over a time frame defined by the user. Other web services include allowing users to share video footages and/or summaries with other parents, caretakers, family, friends, or medical personnel. Another service may allow users to write comments on shared video footages and/or summaries.

Web services module 418 provides machine-to-machine interaction and is operable to communicate services data with client devices 404 and client device 420. Users may log into web services module 418 by identifying an account or device ID of a baby monitor camera system. Client devices 404 and 420 may request services data from web services module 418. Web services module 418 may process the request and provide service data to the requesting devices. Service data includes messages, alerts, statistics, and remote control functions. Services data may be either transmitted along with or independently of broadcast data from cameras 402. For example, client devices 404 may receive broadcast data from cameras 402 via a router on a LAN connection and receive services data from analysis server over a WAN. Alternatively, client devices 402 and 420 may receive both camera broadcast data and services data as a single data stream from web interface 412. Data transmission configurations according to embodiment of the present invention are not limited to the described examples and may include other configurations that allow for camera broadcast data and services data to be received by client devices.

Comparative data database 416 includes comparative data of a given baby over time for movement, temperature, humidity, activities, sleeping behavior, nursing behavior, and any other criteria related to a baby that may change over any given period of time. For example, a map of a baby location over time in a crib, which may be displayed as a thermal image over night and/or over a time frame defined by the user, or as a sequence of thermal images of the baby location in the crib changing over time, can be provided to a user as a service. The comparative data may also include statistics in a comparison to other babies. These statistics may include number of movement, baby measurement (e.g., baby height), baby sleep patterns (including number of times the baby wakes up during the night, the number of hours the baby sleeps, the hours the baby uses to sleep during the day, the number of times the baby self-soothes, and sleep stages during the night (light, deep, REM) in a similar way to other sleep tracking devices), nursing patterns, development stages (e.g., baby rolls over), distance the baby moved, average length of a single movement. The comparative data may be used to display the correlation between baby activities and development stages. Uniform placement and/or configuration of cameras 402 allows for reliable comparison between image sequences of different babies. As such, uniform images may be collected, analyzed, and compared from baby to baby.

Data received from media server 406 may be read into algorithmic logic module 414 to produce analytical outputs, detect events, and calculate statistics. Algorithmic logic module 414 may include logic, memory, and processing components configured to receive the images as well as any other relevant information, process the images using various operations, analyze the processed images, and generate output for segmenting baby movements, detecting baby flips in real time, detecting the crib boundaries, calculating the actual distance between the camera and the baby, detecting baby parts, e.g., hands, head, etc., detecting foreign objects in the crib, detecting if baby's head is covered (e.g., with a blanket), identifying abnormality in baby statistics over time, creating a thermal map of baby's locations in the crib, detecting nursing patterns, detecting sleeping patterns, segmenting sleep stages (light, deep, REM), detecting movement patterns, correlating between activities and development stages, detecting aspiration/reflux/spits up events in real time, detecting abrupt movement patterns in real time, e.g., epilepsy, detecting coughing events, and detecting if the baby leg is stuck in the bars of a crib, to name a few.

The operations on the images may include masking, smoothing, noise reduction, filtering, object recognition, tracking, edge detection, change detection, regression, classification, segmentation, and other computer vision and machine learning methods. The operations may be used to create one or more classifiers, via machine learning, to detect or recognize objects (e.g., blanket, toys, etc.), features (e.g., baby, head, and hands), regions of interest (e.g., baby location), and activity (e.g., sleep/awake status of baby, parental intervention, etc.). Creating the classifiers may include training the classifiers with a training set (or a pool of sample images) including positive and negative examples. For example, positive examples include images with a positive classification while negative examples include images that do not contain an object of interest.

In accordance with one embodiment, classifiers may use the operations to detect the location of a crib within images. Crib detection may be performed once per video (or a first image from a set of image sequences) and using the first image of the video for the remaining images assuming that the crib is stationary. Edges can be detected using an edge detection method such Canny edge detection. Canny edge detection may include applying a Gaussian filter to smooth the image in order to remove the noise, find the intensity gradients of the image, apply non-maximum suppression to eliminate spurious response to edge detection, applying double threshold to determine potential edges (e.g., with high threshold and a low threshold (relative to the highest value of the gradient magnitude of the image), and tracking edges by hysteresis to finalize the detection of edges by suppressing all the other edges that are weak and not connected to strong edges.

According to a further embodiment, classifiers may use the operations to determine a region of interest. The images' regions of interest may generally refer to an area within the images where objects (e.g., the baby) are in the foreground. Detecting the location of the baby within the images may be determined by baby movement. In particular, the region of interest may be an area within the location of a crib where baby activities are be detected. Various techniques may be used to detecting moving objects in videos such as by comparing the difference between a current frame and a reference frame. Samples of video frames of a given baby or of a plurality of babies may be analyzed to detect a general area with these movements. A mask may also be generated to emphasize the foreground by removing small objects from the foreground of an image and placing them in the background.

Head detection may be performed to detect the exact location of the baby's head which is used for analyzing the presence and behavior of the baby. An object detection method such as a Viola & Jones cascade classifier using Histogram of Oriented Gradients (HOG) features can be used. Further description and details of the cascade classifier and HOG features may be found in "Rapid Object Detection Using a Boosted Cascade of Simple Features," by Viola, P., and M. J. Jones, and "Histograms of Oriented Gradients for Human Detection," by Dalal, N., and B. Triggs, which are hereby incorporated by reference in its entirety. Other methods may also be used such as Background model—similar to the ones described in "One Class Background Model", ACCV 2012 Workshops, by Assaf Glazer and Prof. Michael Lindenbaum, and Part-based object detection such as Felzenszwalb's object detection with discriminatively trained part based models, described in "Object Detection with Discriminatively Trained Part Based Models," by Felzenszwalb, P. F., Girshick, R. B., McAllester, D., and Ramanan, D., which are hereby incorporated by reference in its entirety. Similar methods may also be used to detect the hands and torso of the baby.

The detection of parental presence and parental intervention may be useful for certain analyses. Parental presence may generally be defined as when a portion of a parent's head, arm, etc., is within the image, and parental intervention may generally be defined as when a torso or larger portion of a parent's or caretaker's body is within the image such as when the parent/caretaker is tending to a baby in a crib. Detecting parental presence or intervention may include filtering an image to include regions that are not the head, hands, and torso of the baby. Further including detecting the size and presence of a "blob" (the parent/caretaker). A blob may be defined as a region of a digital image in which some properties (e.g., color, intensity, etc.) are constant or vary within a prescribed range of values; all the points in a blob can be considered in some sense to be similar to each other. A parental presence may be distinguished from parental intervention based on the size of the blob. For example, a blob smaller than a given threshold may be identified as a parental presence and a blob larger than the given threshold may be identified as a parental intervention.

Classifiers (and/or operations) may be used as "building blocks" of various analytical processes. For example, a classifier that can determine whether the baby is in the crib or not and a classifier that can detect where the baby's head is may be used in combination to identify a "blanket over the head" condition when determining that a baby is in the crib but a head cannot be located, and raise an alarm. Other analysis may include determining a baby's sleep pattern based on head movement. A region of interest classifier, a head detection classifier, and other operations may be used to determine the number of head movements and their distances to characterize a baby's sleep pattern. Behavioral classification method (such as those described in "A Survey of Vision-Based Methods for Action Representation, Segmentation and Recognition" by Daniel Weinland et-al) can be used to detect event such as moving head from side to side, rolling over, crawling, sitting up, standing, and walking. Further description and details of the sleep patterns based on movement may be found in U.S. Patent Publication No. 2013/0072823, entitled "SLEEP MONITORING SYSTEM," filed on Nov. 13, 2012, which is hereby incorporated by reference in its entirety. Face detection may also be used to determine whether the baby is awake or asleep.

The baby's sleep pattern and/or movements may be compared with other babies. For example, video may be analyzed over various time frames to record the amount of movements and size of movements for comparison to normal and abnormal statistics. The statistics may include statistics collected from analysis of other babies or from a database of public statistics, research and literature. The comparisons may be used to identify healthy baby behavior and signs of illnesses such as autism, infant seizures, etc. Babies may be compared in groups based on age, environments, country, sex, sizes, etc.

FIG. 5 presents an exemplary monitoring interface in accordance with an embodiment of the present invention. The monitoring interface includes video 502 which provides a real time video and data stream of a baby that is monitored by a baby monitor camera system. Along with video 502 includes information 504. Information 504 displays ambient room temperature measured by the baby monitor camera system, time and date. The monitoring interface may allow a user to scroll back in time to see the baby's activities. Playback selections 506 allows for the real time video stream to be paused, rewound, or fast-forwarded.

The monitoring interface also includes message inbox 508, device configuration 510, statistics 512, and alerts 514. Message inbox 508 may include messages from other users (e.g., connected through a social network of other baby monitor camera system users) and messages from service provider or manufacturer of the baby monitor camera system. Device configuration 510 allows for users to change configurations such as camera settings, lighting settings, and remote control of connected appliances. Statistics 512 provide users with various statistics based on analysis of camera broadcast data. For example, statistics may include displaying current temperature and a graph of past measured temperatures, movement over time, sleeping hours, etc. Alerts 514 provide alerts for events such as when the baby will wake, head is covered, climbing, caught in crib, foreign object in crib, and such.

Figure 6:
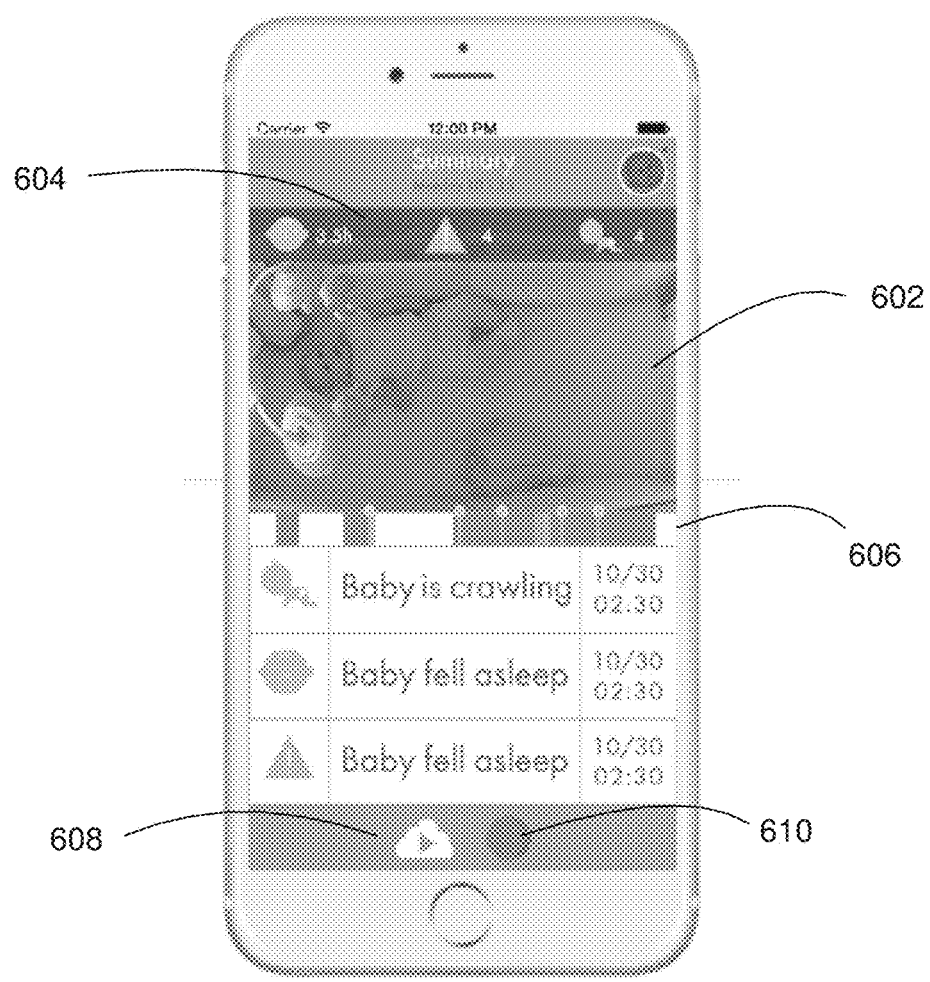
FIG. 6 illustrates an exemplary summary interface on a client device in accordance with an embodiment of the present invention.

FIG. 6 presents an exemplary summary interface on a client device in accordance with an embodiment of the present invention. The summary interface includes video 602 which provides real time and recorded video of a baby that is monitored by a baby monitor camera system. Summary bar 604 includes icons corresponding to certain baby events and alerts such as when the baby is crawling or fell asleep. The icons may be configurable to any other baby events as specified by the user. For each of the icons, the summary bar 604 may also display a count next to each icon. As illustrated, summary bar 604 displays the number of hours the baby went to sleep, the number of times the baby fell asleep, and the number of times the baby was crawling.

The baby events and/or alerts (detected by computer vision and machine learning) may be used to generate video summaries in the form of compressed or shortened clips of real-time video. Parents no longer have to watch hours of video but instead, watch a video summary of their baby for a given period of time (e.g., 4, 8, 12, 24 hours, etc.). The summary video may skip over or omit non-events and inactivity where there are no significant changes in the video frame (which may be determined by computer vision analysis). Video summaries may be shared with friends and family via, for example, social media or email. Summary details 606 may provide a chronological timeline and listing of baby events throughout a given day or specified period of time. According to one embodiment, events in summary details 606 may be selected to retrieve video corresponding to a period of the events. Cloud recording 608 may allow for a user to toggle to and access a recording (full-length or video summary) corresponding to the chronological timeline or any other period of time associated with the summary details 606. Live camera mode 610 allows a user to toggle to a real-time video feed.

FIGS. 1 through 6 are conceptual illustrations allowing for an explanation of the present invention. Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Certain values, thresholds and percentages described herein are merely exemplary and may include other ranges of numbers. Further, the present invention encompasses present and future known equivalents to the known components referred to herein by way of illustration.

It should be understood that various aspects of the embodiments of the present invention could be implemented in hardware, firmware, software, or combinations thereof. In such embodiments, the various components and/or steps would be implemented in hardware, firmware, and/or software to perform the functions of the present invention. That is, the same piece of hardware, firmware, or module of software could perform one or more of the illustrated blocks (e.g., components or steps). In software implementations, computer software (e.g., programs or other instructions) and/or data is stored on a machine readable medium as part of a computer program product, and is loaded into a computer system or other device or machine via a removable storage drive, hard drive, or communications interface. Computer programs (also called computer control logic or computer readable program code) are stored in a main and/or secondary memory, and executed by one or more processors (controllers, or the like) to cause the one or more processors to perform the functions of the invention as described herein. In this document, the terms "machine readable medium," "computer readable medium," "computer program medium," and "computer usable medium" are used to generally refer to media such as a random access memory (RAM); a read only memory (ROM); a removable storage unit (e.g., a magnetic or optical disc, flash memory device, or the like); a hard disk; or the like.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various embodiments of the present invention have been described above, it should be understood that they have been presented by way of example, and not limitation. It would be apparent to one skilled in the relevant art(s) that various changes in form and detail could be made therein without departing from the spirit and scope of the invention. Thus, the present invention should not be limited by any of the above-described exemplary embodiments, but should be defined only in accordance with the following claims and their equivalents.

What is claimed is:

1. A system for monitoring a baby, the system comprising: a camera configured at a predefined working point above a crib to obtain visual output signals from the predefined working point, the camera comprising: a camera housing including a lens, infrared light emitting diodes (IR LED) lights, a sensor, and power and data cabling; wherein the camera utilizes infrared (IR) filters to filter IR light; wherein the IR LED lights include a wavelength of approximately 850 nm to 940 nm such that a red glare is not visible to a baby lying under the camera; wherein the camera housing further includes a lens mount operable for positioning with a rotational adjustment along a horizontal axis relative to the crib; wherein the camera housing is configured to allow the camera to rotate relative to the upper arm; wherein the sensor is configured on the camera to sense intensity of ambient light and infrared light from the IR LED lights; wherein the IR LED light are configured by a processor based on the intensity of ambient light and infrared light from the IR LED lights; and a mount including: an upper arm connected to the camera housing, the upper arm including a first interior conduit configured to receive the power and data cabling of the camera housing; a lower arm connected to the upper arm, the lower arm including a second interior conduit configured to receive the power and the data cabling of the camera housing from the upper arm; and a an attachment configured to attach the mount at the predefined working point above the crib; and a network interface controller configured to: transfer the visual output signals from the predefined working point to an analysis server, the analysis server configured to perform computer vision and machine learning analysis on the visual output signals from the predefined working point, compare the visual output signals and the computer vision and machine learning analysis to comparative data from a database including visual output signals associated with a plurality of babies and computer vision and machine learning analysis of the visual output signals associated with the plurality of babies, determine one or more baby alert events based on the comparison, and transmit messages that identify the determined one or more baby alert events to client devices, wherein the visual output signals associated with the plurality of babies were transferred from one or more second cameras each being configured to attach at one or more second predefined working points above one or more second cribs in uniformity with the predefined working point above the crib of the camera.

2. The system of claim 1 wherein the upper arm includes at least one of speakers, night lights, temperature and humidity sensors.

3. The system of claim 1 wherein the camera housing further includes a lens mount is operable for positioning with a rotational adjustment of 15 degrees of pan along the horizontal axis relative to the crib.

4. The system of claim 1 wherein the camera housing is configured to allow the camera to rotate 15 degrees of pan relative to the upper arm.

5. The system of claim 1 wherein the mount is attached to an outer side of the crib.

6. The system of claim 1 further including a sensitive white night light configured on the top, outer side of the upper arm, and directed away from an underside of the camera and upwards towards a ceiling.

7. The system of claim 1 wherein the mount comprises a universal mount with a bird's-eye view.

8. The system of claim 1, wherein the camera is configured to transfer the visual output signals to client devices over a local area network.

9. The system of claim 1, wherein the camera is configured to transfer visual output signals to the analysis server over a web-based network connected to a centralized computation and storage center.

10. The system of claim 1, the camera and the predefined working point are substantially the same for monitoring different babies.

11. The system of claim 1, wherein the analysis server is further operable to:
generate notifications based on the computer vision and machine learning analysis; and
transmit the notifications to the client devices.

12. The system of claim 11, wherein the notifications include baby waking up, baby falling asleep, baby self-soothes.

13. The system of claim 1, wherein the analysis server is further operable to:
generate alerts based on the computer vision and machine learning analysis; and
transmit the alerts based on the computer vision and machine learning analysis.

14. The system of claim 13, wherein the alerts include baby rolled over, baby is crying, baby is climbing, baby spits up, foreign object in crib, aspiration event, flip event, seizures event, leg stuck event, and head covered event.

15. The system of claim 1, wherein the analysis server is further operable to perform computer vision and machine learning processing on the visual output signals as part of performing the computer vision and machine learning analysis on the visual output signals.

16. The system of claim 15, wherein the computer vision and machine learning processing includes at least one of background subtraction algorithms, baby region of interest detection, head detection processes, parental intervention detection, action rectangle identification, behavioral classification, hands detection, and baby presence detection methods.

* * * * *